(12) United States Patent
Nathanson et al.

(10) Patent No.: US 8,043,243 B2
(45) Date of Patent: Oct. 25, 2011

(54) KNEE BRACE HINGES HAVING DUAL AXES OF ROTATION

(75) Inventors: Jeremy J. Nathanson, San Clemente, CA (US); Richard E. Gildersleeve, Carlsbad, CA (US)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 11/030,276

(22) Filed: Jan. 6, 2005

(65) Prior Publication Data

US 2005/0148915 A1    Jul. 7, 2005

Related U.S. Application Data

(60) Provisional application No. 60/534,753, filed on Jan. 7, 2004.

(51) Int. Cl.
  *A61F 5/01* (2006.01)
(52) U.S. Cl. .......................... 602/23; 602/26
(58) Field of Classification Search .................... 602/16, 602/23, 27, 26, 5, 20–22, 25, 28, 29; 16/357, 16/358, 368, 369, 371, 374
  See application file for complete search history.

(56) References Cited

U.S. PATENT DOCUMENTS

| | | |
|---|---|---|
| 3,581,741 A | 6/1971 | Rosman |
| 3,779,654 A | 12/1973 | Horne |
| 3,799,158 A | 3/1974 | Gardner |
| 3,817,244 A | 6/1974 | Taylor |
| 3,826,251 A | 7/1974 | Ross |
| 3,901,223 A | 8/1975 | May |
| 3,902,482 A | 9/1975 | Taylor |
| 4,241,730 A | 12/1980 | Helfet |
| 4,245,629 A | 1/1981 | Cummins |
| 4,256,097 A | 3/1981 | Willis |
| 4,320,747 A | 3/1982 | Daniell, Jr. |
| 4,337,764 A | 7/1982 | Lerman |
| 4,353,361 A | 10/1982 | Foster |
| 4,361,142 A * | 11/1982 | Lewis et al. ................. 602/16 |
| 4,372,298 A | 2/1983 | Lerman |
| 4,379,463 A | 4/1983 | Meier et al. |

(Continued)

FOREIGN PATENT DOCUMENTS

DE        40 13 693        8/1991

(Continued)

OTHER PUBLICATIONS

DonJoy (dj ortho); 1988 Bracing Catalogue; Catalog; 20 pages; 1988.

*Primary Examiner* — Danton DeMille
(74) *Attorney, Agent, or Firm* — Ropes & Gray LLP

(57) ABSTRACT

Disclosed is a knee brace that incorporates hinges that allow the brace to pivot simultaneously about a flexion-extension axis and a longitudinal rotation axis as the brace flexes and/or extends. The hinges include a medial hinge and a lateral hinge. The medial hinge defines a medial pivot axis and the lateral hinge defines a lateral pivot axis. The medial pivot axis does not coincide with the lateral pivot axis, and neither axis coincides with the flexion-extension axis. Calf portions of each hinge are pivotable with respect to their respective uprights about an axis that is substantially parallel to the longitudinal rotation axis. The pivotability of the calf portions with respect to the calf frame eliminates stresses that would otherwise develop in the hinges as the brace flexes and/or extends.

9 Claims, 8 Drawing Sheets

U.S. PATENT DOCUMENTS

| | | | |
|---|---|---|---|
| 4,387,709 A | 6/1983 | Shen | |
| 4,393,542 A | 7/1983 | Martinez | |
| 4,428,369 A | 1/1984 | Peckham et al. | |
| 4,433,679 A | 2/1984 | Mauldin et al. | |
| 4,463,751 A | 8/1984 | Bledsoe | |
| 4,489,718 A | 12/1984 | Martin | |
| 4,493,316 A | 1/1985 | Reed et al. | |
| 4,520,802 A | 6/1985 | Mercer et al. | |
| 4,554,913 A | 11/1985 | Womack et al. | |
| 4,599,998 A | 7/1986 | Castillo | |
| 4,602,627 A | 7/1986 | Vito et al. | |
| D286,183 S | 10/1986 | Womack et al. | |
| 4,620,532 A * | 11/1986 | Houswerth | 602/16 |
| 4,624,247 A | 11/1986 | Ford | |
| 4,655,201 A * | 4/1987 | Pirmantgen | 602/16 |
| 4,699,129 A | 10/1987 | Aaserude et al. | |
| 4,732,143 A | 3/1988 | Kausek et al. | |
| 4,733,656 A | 3/1988 | Marquette | |
| 4,751,920 A | 6/1988 | Mauldin et al. | |
| 4,768,500 A * | 9/1988 | Mason et al. | 602/26 |
| 4,771,768 A * | 9/1988 | Crispin | 602/16 |
| 4,773,404 A | 9/1988 | Townsend | |
| 4,802,467 A | 2/1989 | Pansiera | |
| 4,821,707 A | 4/1989 | Audette | |
| 4,856,501 A | 8/1989 | Castillo et al. | |
| 4,865,024 A | 9/1989 | Hensley et al. | |
| 4,928,676 A | 5/1990 | Pansiera | |
| 4,940,044 A | 7/1990 | Castillo | |
| 4,962,760 A * | 10/1990 | Jones | 602/27 |
| 4,986,264 A | 1/1991 | Miller | |
| 5,009,223 A | 4/1991 | DeFonce | |
| 5,022,391 A | 6/1991 | Weidenburner | |
| 5,044,360 A | 9/1991 | Janke | |
| 5,063,916 A | 11/1991 | France et al. | |
| 5,074,290 A | 12/1991 | Harris et al. | |
| 5,078,127 A | 1/1992 | Daneman et al. | |
| 5,086,760 A | 2/1992 | Neumann et al. | |
| 5,094,232 A | 3/1992 | Harris et al. | |
| 5,107,824 A | 4/1992 | Rogers et al. | |
| 5,230,696 A | 7/1993 | Silver et al. | |
| 5,244,455 A | 9/1993 | Swicegood et al. | |
| 5,277,698 A | 1/1994 | Taylor | |
| 5,292,303 A | 3/1994 | Bastyr et al. | |
| 5,302,169 A | 4/1994 | Taylor | |
| 5,356,370 A | 10/1994 | Fleming | |
| RE34,818 E | 1/1995 | Daneman et al. | |
| 5,399,149 A | 3/1995 | Frankowiak et al. | |
| 5,400,806 A | 3/1995 | Taylor | |
| 5,421,810 A | 6/1995 | Davis et al. | |
| 5,437,619 A | 8/1995 | Malewicz et al. | |
| 5,443,444 A * | 8/1995 | Pruyssers | 602/26 |
| 5,542,774 A | 8/1996 | Hoy | |
| 5,586,970 A | 12/1996 | Morris et al. | |
| 5,611,774 A | 3/1997 | Postelmans et al. | |
| 5,632,725 A | 5/1997 | Silver et al. | |
| 5,658,243 A | 8/1997 | Miller et al. | |
| 5,792,086 A | 8/1998 | Bleau et al. | |
| 5,921,946 A | 7/1999 | Tillinghast et al. | |
| 6,001,075 A * | 12/1999 | Clemens et al. | 602/16 |
| 6,074,355 A | 6/2000 | Bartlett | |
| 6,309,368 B1 | 10/2001 | Herzberg et al. | |
| 6,387,066 B1 | 5/2002 | Whiteside | |
| 6,402,711 B1 | 6/2002 | Nauert | |
| 6,793,641 B2 | 9/2004 | Freeman et al. | |
| 6,953,442 B2 * | 10/2005 | Yamasaki et al. | 602/22 |
| 6,969,364 B2 * | 11/2005 | Sterling | 602/16 |
| 7,044,925 B2 | 5/2006 | Castillo et al. | |
| 7,201,728 B2 | 4/2007 | Sterling | |
| 2004/0054311 A1 | 3/2004 | Sterling | |
| 2005/0148915 A1 | 7/2005 | Nathanson et al. | |
| 2005/0148916 A1 | 7/2005 | Nathanson | |

FOREIGN PATENT DOCUMENTS

| | | |
|---|---|---|
| EP | 0 361 405 | 4/1990 |
| WO | WO 98/14144 | 4/1998 |
| WO | WO 01/10360 A1 | 2/2001 |

* cited by examiner

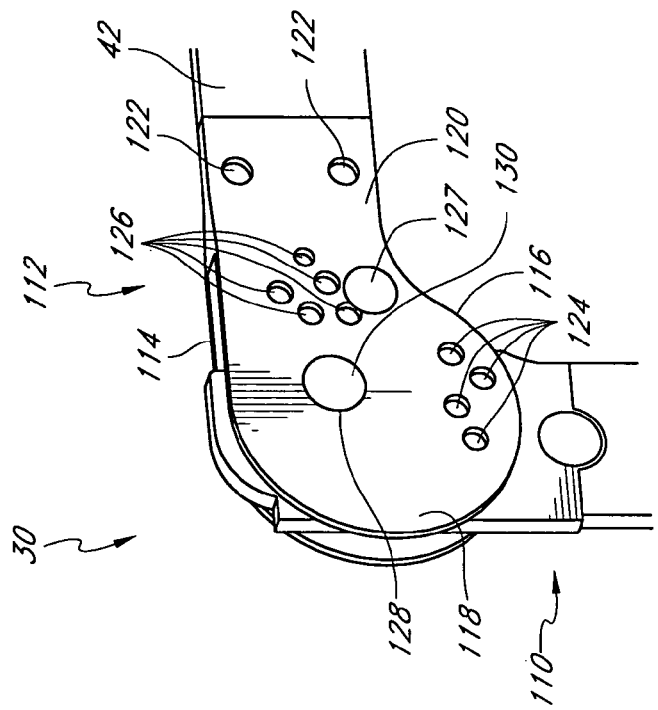
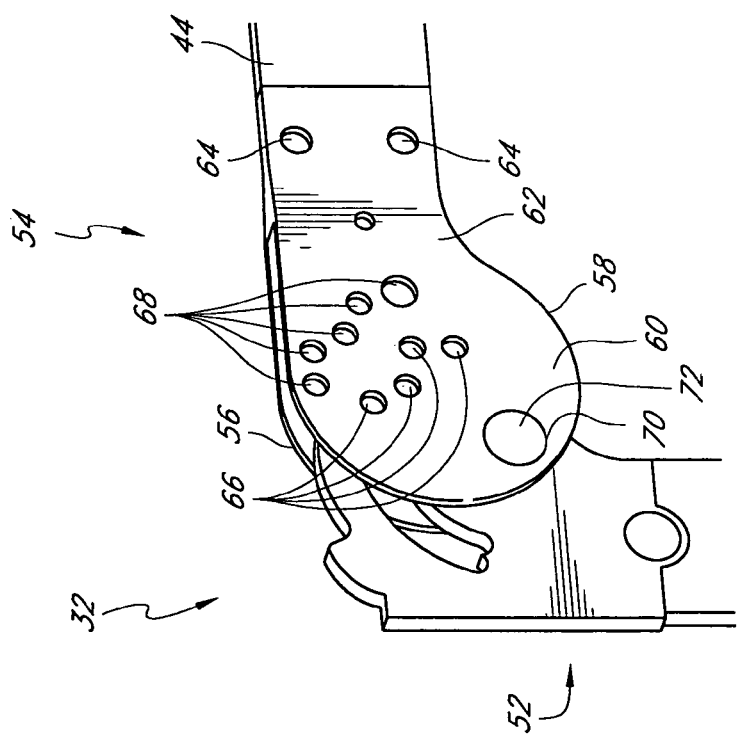
FIG. 4
FIG. 3

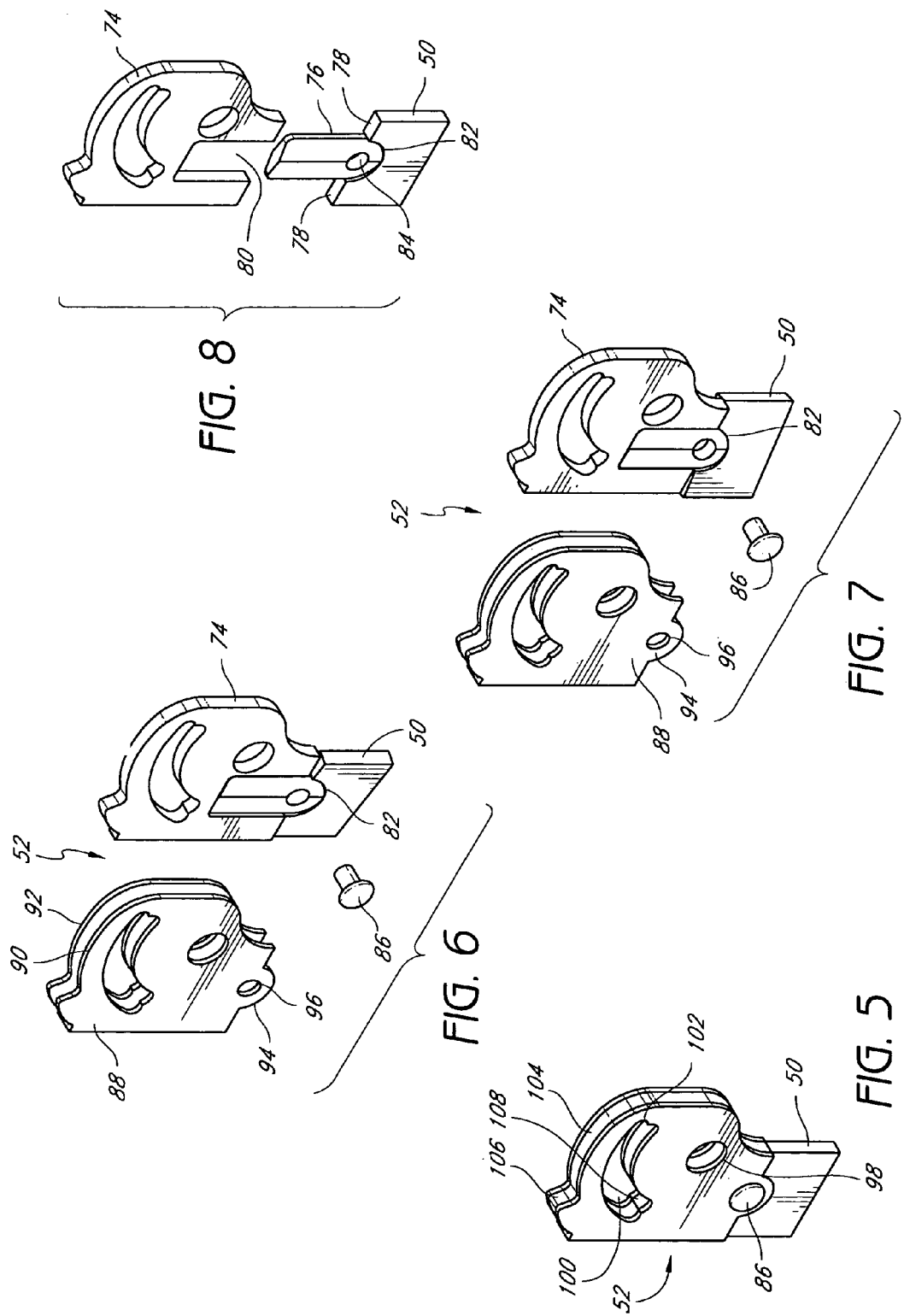

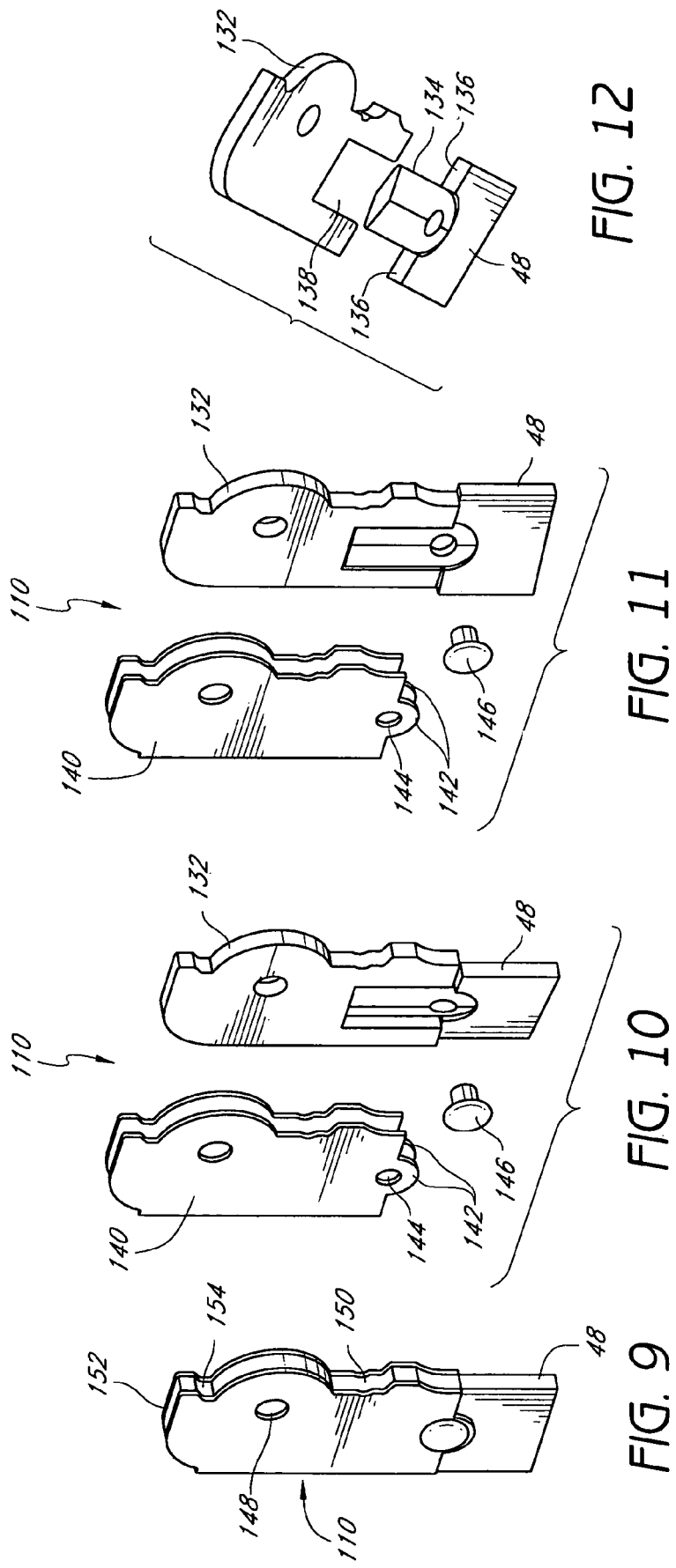

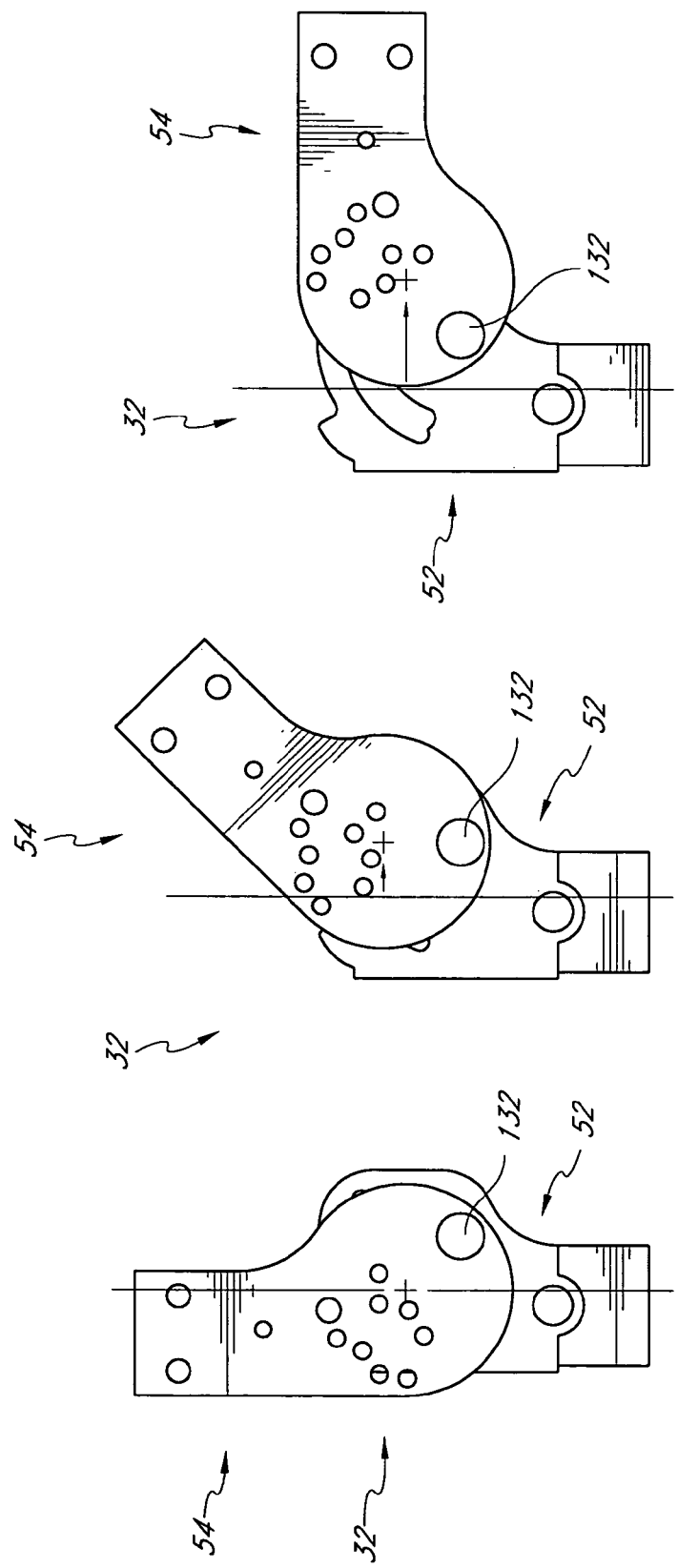

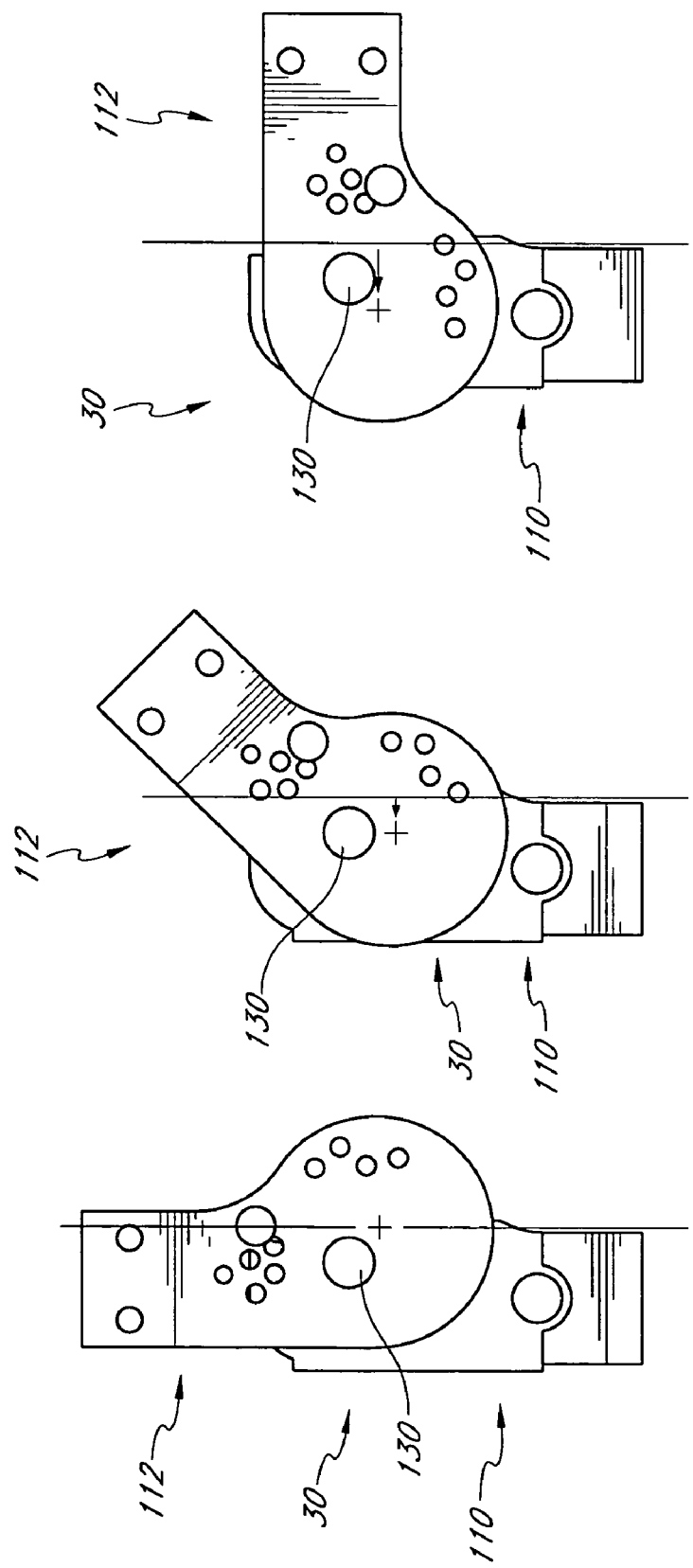

KNEE BRACE HINGES HAVING DUAL AXES OF ROTATION

RELATED APPLICATION

This application claims priority to provisional application Ser. No. 60/534,753, filed on Jan. 7, 2004, the entire contents of which are hereby expressly incorporated by reference.

BACKGROUND OF THE INVENTION

1. Field of the Invention

The present invention relates to orthopedic bracing.

2. Description of the Related Art

Two functions that knee brace hinges perform are guiding the wearer's knee along a natural path of motion, and restraining the wearer's knee against unnatural and harmful motions. In order to accomplish these functions, many knee brace hinge designs attempt to mimic the natural motion of the knee. Some of these designs include monocentric hinges, polycentric hinges, four-bar-linkage hinges, and cam hinges.

The human knee, however, follows a rather complex path as it flexes and extends. In general, when viewed in the sagittal plane, the knee moves in a slide-and-glide fashion in which the femur partially rolls back posteriorly on the tibia as the knee flexes. Most of the motion of the knee occurs in the sagittal plane. However, a not insignificant amount of knee motion also occurs out of this two-dimensional perspective, as explained in detail below.

Many researchers have attempted to measure and model the three-dimensional motion of the knee. Based on this research, many designers have constructed knee brace hinges that approximate this three-dimensional motion. For example, U.S. Pat. Nos. 5,107,824, 5,611,774 and 5,792,086 describe three such hinges. These designs are all of the cam-slot type and include curved plates. The cam-slot arrangement allows for the hinge to undergo complex motion patterns and the curved plates allow for rotations to occur outside of the sagittal plane. However, these designs have a number of drawbacks.

First, cam-slot hinges require long cavities to be cut within the hinge plates. These cavities often result in large, bulky hinges, and leave little room for other features such as extension and flexion control stops. Second, curved hinge plates are costly to manufacture as compared to flat plates, which can often be made by inexpensive processes such as sheet metal stamping. Third, the curvature of the hinge plates in these designs is based upon the spacing between the medial and lateral hinges. This spacing changes with the size of the patient wearing the brace. Thus, to meet the needs of differently sized patients, a variety of sizes and shapes of curved parts must be manufactured. If the hinges are not properly sized and shaped, the hinges may not operate smoothly through their range of motion.

Recent research has revealed that the three-dimensional motion of the human knee can be described as a simultaneous rotation about two axes, each of which is fixed relative to the leg bones. (Churchill, *Clinical Orthopaedics and Related Research*, No. 356, pp. 111-118, 1998.). The first axis is the familiar flexion-extension axis. This axis is fixed relative to the femur, extends in the medial-lateral direction, and runs through the lateral and medial epicondyles of the femur bone. The second axis is the tibial rotation axis (also referred to as the longitudinal rotation axis). This axis is fixed relative to the tibia, runs parallel to the length of the tibia, and is located slightly medial to the center of the tibial plateau. In general, as the knee flexes the tibia simultaneously rotates internally about the tibial rotation axis.

SUMMARY OF THE INVENTION

The preferred embodiments of the present knee brace hinges having dual axes of rotation have several features, no single one of which is solely responsible for their desirable attributes. Without limiting the scope of these knee brace hinges as expressed by the claims that follow, their more prominent features will now be discussed briefly. After considering this discussion, and particularly after reading the section entitled "Detailed Description of the Preferred Embodiments," one will understand how the features of the preferred embodiments provide advantages, which include the ability to track natural motion of the knee according to the dual axis of rotation model, while at the same time restraining the knee against harmful motions.

One embodiment of the present knee brace hinges having dual axes of rotation comprises an orthopedic knee brace. The brace comprises a medial hinge defining a medial pivot axis, and a lateral hinge defining a lateral pivot axis. The medial and lateral pivot axes do not coincide with one another.

Another embodiment of the present knee brace hinges having dual axes of rotation comprises an orthopedic knee brace. The brace comprises a rigid thigh frame, and a rigid calf frame. The thigh frame and calf frame are adapted to pivot relative to one another simultaneously about a substantially horizontal flexion-extension axis and a substantially vertical longitudinal rotation axis as the brace flexes and/or extends.

Another embodiment of the present knee brace hinges having dual axes of rotation comprises an orthopedic knee brace. The brace comprises a rigid frame including at least one of a rigid medial upright and a rigid lateral upright. The brace further comprises a hinge, the hinge including a portion secured to an end of the at least one upright. The hinge portion is adapted to pivot relative to the frame about an axis that is substantially perpendicular to a flexion-extension axis of the brace.

Another embodiment of the present knee brace hinges having dual axes of rotation comprises a hinge adapted for use in an orthopedic knee brace. The hinge comprises a calf portion including a main plate portion and a sleeve portion. The sleeve portion receives the main plate portion between first and second panels thereof.

Another embodiment of the present knee brace hinges having dual axes of rotation comprises a method of supporting a knee in order to allow the knee to flex and extend in a natural manner, while restraining the knee against harmful motions. The method comprises the step of applying to the knee an orthopedic knee brace including a rigid thigh frame and a rigid calf frame, wherein the thigh frame and calf frame are adapted to pivot relative to one another simultaneously about a substantially horizontal flexion-extension axis and a substantially vertical longitudinal rotation axis as the brace flexes and/or extends.

Another embodiment of the present knee brace hinges having dual axes of rotation comprises a method of supporting a knee in order to allow the knee to flex and extend in a natural manner, while restraining the knee against harmful motions. The method comprises the step of applying to the knee an orthopedic knee brace including a medial hinge defining a medial pivot axis, and a lateral hinge defining a lateral pivot axis, wherein the medial and lateral pivot axes do not coincide with one another.

BRIEF DESCRIPTION OF THE DRAWINGS

The preferred embodiments of the present knee brace hinges having dual axes of rotation, illustrating their features, will now be discussed in detail. These embodiments depict the novel and non-obvious knee brace hinges shown in the accompanying drawings, which are for illustrative purposes only. These drawings include the following figures, in which like numerals indicate like parts:

FIG. 3 is a left-side perspective view of the lateral hinge of FIG. 1;

FIG. 4 is a left-side perspective view of the medial hinge of FIG. 1;

FIG. 5 is a left-side perspective view of components of the hinge of FIG. 3;

FIG. 6 is an exploded left-side perspective view of the hinge components FIG. 5;

FIG. 7 is an exploded left-side perspective view of the hinge components of FIG. 5;

FIG. 8 is an exploded left-side perspective view of some of the hinge components of FIG. 5;

FIG. 9 is a left-side perspective view of components of the hinge of FIG. 4;

FIG. 10 is an exploded left-side perspective view of the hinge components of FIG. 9;

FIG. 11 is an exploded left-side perspective view of the hinge components of FIG. 9;

FIG. 12 is an exploded left-side perspective view of some of the hinge components of FIG. 9;

FIG. 13 is a left-side elevational view of the lateral hinge of FIG. 3;

FIG. 14 is a left-side elevational view of the hinge of FIG. 3;

FIG. 15 is a left-side elevational view of the hinge of FIG. 3;

FIG. 16 is a left-side elevational view of the medial hinge of FIG. 4;

FIG. 17 is a left-side elevational view of the hinge of FIG. 4;

FIG. 18 is a left-side elevational view of the hinge of FIG. 4;

DETAILED DESCRIPTION OF THE PREFERRED EMBODIMENTS

As used herein, the term lateral means away from a vertical centerline of the body, the term medial means toward a vertical centerline of the body, the term anterior means toward the front of the body, the term posterior means toward the back of the body, the term superior means higher up on the body, and the term inferior means inferior on the body. Each of the above terms, as applied to components of the brace 34, refer to the configuration of the brace 34 shown in FIG. 1, which the brace 34 occupies when the wearer's leg is at full extension and the wearer is standing. For clarity, the wearer's leg is not illustrated.

Figure 2:
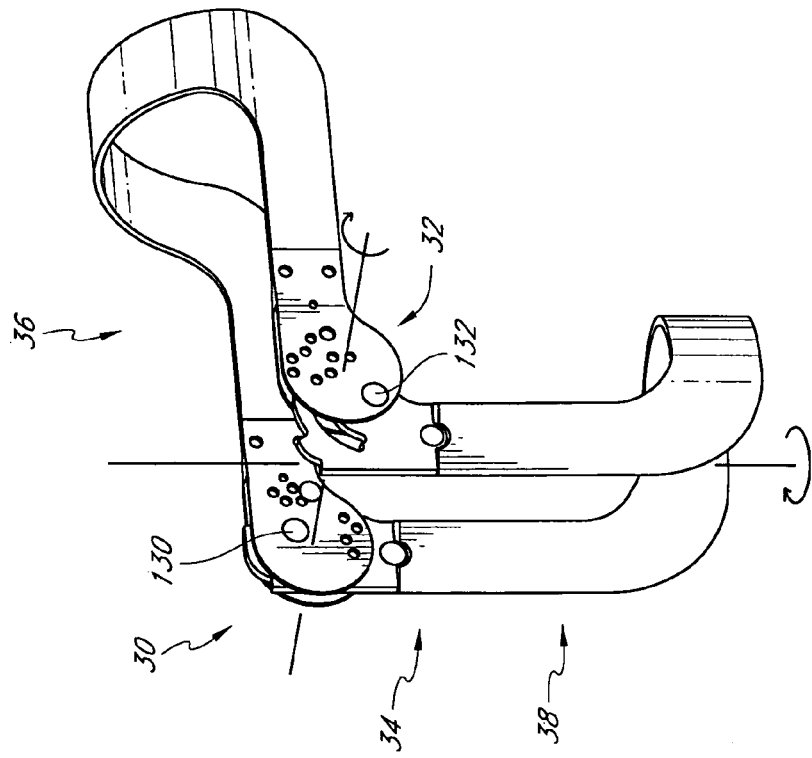
FIG. 2 is a left-side perspective view of the brace of FIG. 1.
Figure 1:
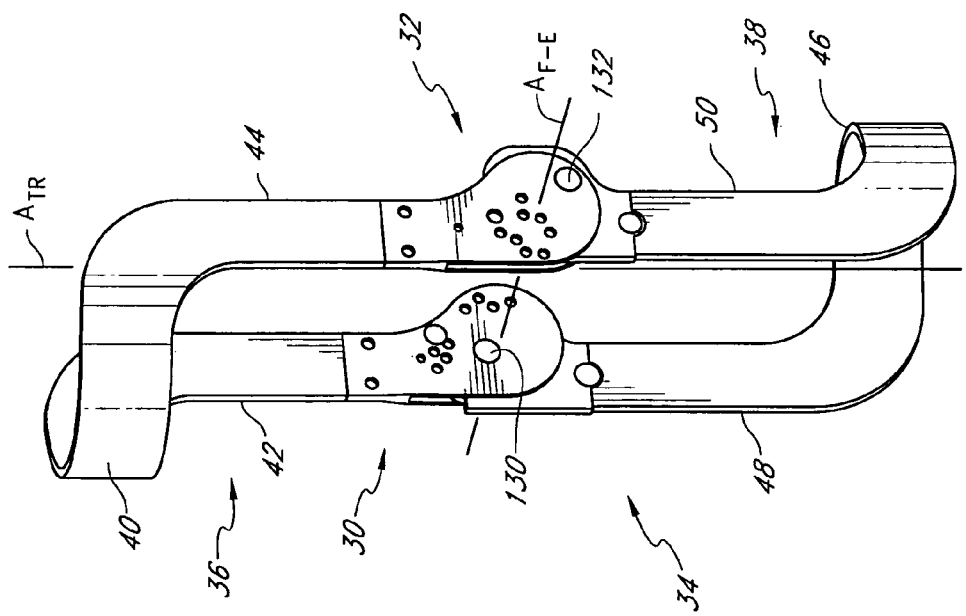
FIG. 1 is a left-side perspective view of a brace including one embodiment of the present knee brace hinges having dual axes of rotation.

One embodiment of the present knee brace 34 hinges 30, 32, illustrated in FIGS. 1 and 2, approximates the motion of the human knee based on the dual axis of rotation model, which is described above. Thus, the hinges 30, 32 incorporate coupled motions about the flexion-extension axis $A_{F-E}$ and the tibial rotation axis $A_{TR}$. In order to achieve this type of motion, as the wearer's knee flexes the medial side of the thigh frame 36 moves anteriorly relative to the calf frame 38 (FIGS. 3-5), and the lateral side of the thigh frame 36 moves posteriorly relative to the calf frame 38 (FIGS. 6-8). Additionally, since the tibial rotation axis $A_{TR}$ is located nearer the medial side of the wearer's knee, the lateral hinge 32 has a larger translation component as compared to the medial side (FIGS. 3-8). As the wearer's knee extends, the motion described above is reversed.

With reference to FIGS. 1 and 2, one embodiment of the hinges 30, 32 is illustrated within a knee brace 34 comprising a superior frame 36, or thigh frame 36, and an inferior frame 38, or calf frame 38. The illustrated brace 34 is adapted to be worn on the wearer's left leg. Those of skill in the art will appreciate that a brace having a reverse configuration would be adapted to be worn on the wearer's right leg. The illustrated brace 34 is not intended to be limiting.

With continued reference to FIG. 1, in one embodiment the thigh frame 36 and calf frame 38 may each comprise a unitary length of rigid material, such as a metal or a composite. Alternatively, each frame may be constructed of multiple pieces that are secured to one another. The thigh frame 36 includes a superior transverse portion 40 that is adapted to extend across an anterior portion of the wearer's thigh. A medial thigh upright 42 and a lateral thigh upright 44 each extend downward from the superior transverse portion 40. The uprights 42, 44 extend along the medial and lateral sides, respectively, of the wearer's thigh when the brace 34 is worn. The calf frame 38 includes an inferior transverse portion 46 that is adapted to extend across a posterior portion of the wearer's calf. A medial calf upright 48 and a lateral calf upright 50 each extend upward from the inferior transverse portion 46. The uprights 48, 50 extend along the medial and lateral sides, respectively, of the wearer's calf when the brace 34 is worn.

In one embodiment, the brace 34 is positioned on the wearer's leg (not shown) such that the medial hinge 30 is positioned adjacent the medial side of the wearer's knee, and the lateral hinge 32 is positioned adjacent the lateral side of the wearer's knee. A plurality of straps (not shown) anchors the brace 34 to the leg.

With reference to FIG. 3, the illustrated lateral hinge 32 includes a calf portion 52 and a thigh portion 54. The thigh portion 54 includes a first hinge plate 56 and a second hinge plate 58. The hinge plates 56, 58 are spaced from one another along the medial-lateral axis, with the first hinge plate 56 being located relatively closer to the wearer's knee, and the second hinge plate 58 being located relatively farther from the wearer's knee. The space between the first and second hinge plates 56, 58 receives the calf portion 52. The hinge plates 56, 58 are substantially identical to one another, and each includes a substantially circular inferior portion 60 with an elongate superior portion 62 extending therefrom. The hinge plates 56, 58 are preferably constructed of a sturdy material, such as a metal.

Each of the hinge plates 56, 58 is secured to an inferior end of the lateral upright 44 on the thigh frame 36. The superior portion 62 of each hinge plate 56, 58 includes first and second securement apertures 64. The securement apertures 64 are adapted to receive fastening members (not shown), such as bolts or rivets, that may be used to secure the hinge plates 56, 58 to the lateral upright 44 on the thigh frame 36. Those of skill in the art will appreciate that the hinge plates 56, 58 may be secured to the lateral upright 44 in a variety of other ways, such as with fastening members (such as bolts or rivets, for example), adhesive, welds, insert molding, etc. The exact method of attachment is immaterial to the functioning of the present hinges 30, 32.

With continued reference to FIG. 3, the inferior portions 60 of the illustrated hinge plates 56, 58 further comprise a plurality of flexion stop apertures 66, and a plurality of extension stop apertures 68. Each of the stop apertures 66, 68 is adapted to receive a stop member (not shown), such as a pin. The stop member(s) may be removable and reinsertable with respect to the stop apertures 66, 68, or they may be permanently secured within the stop apertures 66, 68. As described in more detail below, the flexion stop member engages a flexion stop surface on the calf portion 52 to define a maximum angle of flexion for the lateral hinge 32. As also described in more detail below, the extension stop member engages an extension stop surface on the calf portion to define a maximum angle of extension for the lateral hinge 32.

The inferior portions 60 of the illustrated hinge plates 56, 58 further comprise a pivot aperture 70. A pivot member 72, such as a pin or rivet, extends through the pivot apertures 70 to secure the thigh portion 54 to the calf portion 52, as described in more detail below.

With reference to FIGS. 5-8, the calf portion 52 includes a main plate portion 74 that is pivotably secured to a superior end of the lateral upright 50 on the calf frame 38. With specific reference to FIG. 8, the superior end of the lateral upright includes a projection 76 that is centered on an anterior-posterior centerline of the upright 50. First and second flat shoulders 78 flank either side of the projection 76. The projection 76 is received within a substantially U-shaped recess 80 in an inferior end of the main plate portion 74. The projection 76 is shaped as a faceted bar. In the illustrated embodiment, the projection 76 has a diamond-shaped cross-section. A width of the projection 76 is slightly less than a width of the recess 80 in the main plate portion 74. The main plate portion 74 is thus pivotable atop the lateral upright 50 about a longitudinal axis of the upright 50, as shown in FIGS. 6 and 7. The ability of the main plate portion 74 to pivot with respect to the lateral upright 50 contributes to the ability of the present hinges 30, 32 to mimic the dual axis of rotation model of knee joint motion, as explained in greater detail below.

With further reference to FIG. 8, an inferior end of the projection is semi-circular and seats in a semi-circular indentation 82 in the superior end of the lateral upright 50. The lateral upright 50 and the projection 76 are preferably unitary in construction, but could be fabricated as separate pieces secured to one another. The inferior end includes an aperture 84 that receives a fastening member 86 (FIGS. 5-7), as described in detail below. A maximum thickness of the projection 76, which is located at the anterior-posterior center of the projection 76, is substantially equal to a thickness of the adjoining portion of the lateral upright 50. The thickness of the projection 76 tapers downward at a constant rate in both the anterior and posterior directions from the location of the maximum thickness.

With reference to FIGS. 6 and 7, a sleeve 88 fits over the main plate portion 74. The sleeve 88 includes a first panel 90 and a second panel 92 that are spaced from one another and joined along one edge of each. A perimeter shape of each panel 90, 92 is substantially identical to the perimeter shape of the main plate portion 74. A spacing between the first and second panels 90, 92 is substantially equal to a thickness of the main plate portion 74. The sleeve 88 is thus configured to receive the main plate portion 74, as shown in FIG. 5. The sleeve 88 is preferably constructed of a sturdy material, such as a metal (e.g., steel or aluminum) or certain plastics.

With continued reference to FIGS. 6 and 7, an inferior end of each panel 90, 92 includes a semi-circular tab 94 of substantially the same dimensions as the semi-circular indentations 82 in the superior end of the lateral upright 50. An aperture 96 straddles the junction of each tab 94 and its respective panel 90, 92. The tabs 94 and apertures 96 are sized and located so as to coincide with the indentations 82 and aperture 84, respectively, on the lateral upright 50 when the sleeve 88 is fitted onto the main plate portion 74. In this configuration, the apertures 84, 96 receive the fastening member 86, such as a pin or rivet, that secures the sleeve 88 to the projection 76, as illustrated in FIG. 5. With the sleeve 88 in place, the faceted projection 76 defines the rotational limits of the calf-portion 52 of the hinge 32 with respect to the lateral upright 50. As the calf-portion 52 reaches either of its rotational limits, the inner surfaces of the panels 90, 92 contact the non-adjacent facets of the projection 76, halting further rotation of the calf-portion 52 in that direction.

With reference to FIG. 5, the lateral calf portion 52 includes a pivot aperture 98 that is located in a posterior portion at approximately a superior-inferior center thereof. The pivot aperture 98 is coaxial with the pivot apertures 70 in the lateral thigh portions 56, 58 (FIG. 3). The fastening member 72, such as a pin or a rivet, passes through all of the coaxial apertures 70, 98 to pivotably secure the thigh portion 54 to the calf portion 52, as shown in FIG. 3.

With further reference to FIG. 5, the calf portion 52 further includes an arcuately-shaped channel 100 that is spaced from the pivot aperture 98. The illustrated channel 100 extends along an arc of approximately 75°, and is located both superiorly and anteriorly of the pivot aperture 98. Those of skill in the art will appreciate that the arc traced by the channel 100 could be less or more than approximately 75°. The flexion stop apertures 66 on the thigh portion 54 (FIG. 3) trace the arc as the calf and thigh portions 52, 54 rotate relative to one another about the pivot member 72. A posterior end 102 (FIG. 5) of the channel 100 provides a flexion stop surface 102. Thus, if a flexion stop member is disposed in one of the flexion stop apertures 66, contact between that flexion stop member and the flexion stop surface 102 limits further flexion of the hinge 32. In the illustrated embodiment, a plurality of flexion stop apertures 66 are provided so that the maximum flexion angle of the hinge 32 can be adjusted as desired by removing the flexion stop member from a first aperture 66 and disposing it within another aperture 66. For example, the flexion stop apertures 66 may be positioned to provide maximum flexion angles of 45°, 60°, 75° and 90°.

With further reference to FIG. 5, a superior edge 104 of the calf portion 52 includes a shoulder 106 that faces substantially in the posterior direction. The shoulder 106 provides an extension stop surface 106. Thus, if an extension stop member is disposed in one of the extension stop apertures 68 on the thigh portion 54 (FIG. 3), contact between that extension stop member and the extension stop surface 106 limits further extension of the hinge 32. In the illustrated embodiment, a plurality of extension stop apertures 68 are provided so that the maximum extension angle of the hinge 32 can be adjusted as desired by removing the extension stop member from a first aperture 68 and disposing it within another aperture 68. For example, the extension stop apertures 68 may be positioned to provide maximum extension angles of 40°, 30°, 20°, 10° and 0°. An anterior end 108 of the channel 100 also provides an extension stop surface 108 that may engage a stop member positioned within one of the flexion stop apertures 68.

With reference to FIG. 4, the illustrated medial hinge 30 includes a calf portion 110 and a thigh portion 112. The thigh portion 112 includes a first hinge plate 114 and a second hinge plate 116. The hinge plates 114, 116 are spaced from one another along the medial-lateral axis, with the first hinge plate 114 being located relatively closer to the wearer's knee, and the second hinge plate 116 being located relatively farther from the wearer's knee. The space between the first and second hinge plates 114, 116 receives the calf portion 110. The hinge plates 114, 116 are substantially identical to one another, and each includes a substantially circular inferior portion 118 with an elongate superior portion 120 extending therefrom. The hinge plates 114, 116 are preferably constructed of a sturdy material, such as a metal.

Each of the hinge plates 114, 116 is secured to an inferior end of the medial upright 42 on the thigh frame 36. The superior portion 120 of each hinge plate 114, 116 includes first and second securement apertures 122. The securement apertures 122 are adapted to receive fastening members (not shown), such as bolts or rivets, that may be used to secure the hinge plates 114, 116 to the medial upright 42 on the thigh frame 36. Those of skill in the art will appreciate that the hinge plates 114, 116 may be secured to the medial upright 42 in a variety of other ways, such as with fastening members (such as bolts or rivets, for example), adhesive, welds, insert molding, etc. The exact method of attachment is immaterial to the functioning of the present hinges 30, 32.

With continued reference to FIG. 4, the inferior portions 118 of the illustrated hinge plates 114, 116 further comprise a plurality of flexion stop apertures 124, and a plurality of extension stop apertures 126. Each of the stop apertures 124, 126 is adapted to receive a stop member 127, such as a pin. The stop member(s) 127 may be removable and reinsertable with respect to the stop apertures 124, 126, or they may be permanently secured within the stop apertures 124, 126. As described in more detail below, the flexion stop member engages one of a plurality of flexion stop surfaces on the calf portion 110 to define a maximum angle of flexion for the hinge 30. As also described in more detail below, the extension stop member engages an extension stop surface on the calf portion 110 to define a maximum angle of extension for the hinge 30.

The inferior portions 118 of the illustrated hinge plates 114, 116 further comprise a pivot aperture 128. A pivot member 130, such as a pin or rivet, extends through the pivot apertures 128 to secure the thigh portion 112 to the calf portion 110, as described in more detail below.

With reference to FIGS. 9-12, the calf portion 110 includes a main plate portion 132 that is pivotably secured to a superior end of the medial upright 48 on the calf frame 38. With specific reference to FIG. 12, the superior end of the medial upright 48 includes a faceted projection 134 that is centered on an anterior-posterior centerline of the upright 48. First and second flat shoulders 136 flank either side of the projection 134. The projection 134 is received within a substantially U-shaped recess 138 in an inferior end of the main plate portion 132. The projection 134 and recess 138 are sized and shaped similarly to the corresponding components of the lateral hinge 32. Further, the medial calf portion 110 includes a sleeve 140 with tabs 142 and apertures 144, and a fastening member 146 that secures the sleeve 140 to the main plate portion 132. All of these components are configured similarly to the corresponding components of the lateral hinge 32. Accordingly, the configuration and function of these components will not be repeated here, except to note that the main plate portion 132 is pivotable atop the medial upright 48 about a longitudinal axis of the upright 48, as shown in FIGS. 10 and 11. The ability of the main plate portion 132 to pivot with respect to the medial upright 48 contributes to the ability of the present hinges 30, 32 to mimic the dual axis of rotation model of knee joint motion, as explained in greater detail below. Finally, the perimeter shape of the sleeve 140 is substantially identical to the perimeter shape of the main plate portion 132.

With particular reference to FIG. 9, the medial calf portion 110 includes a pivot aperture 148 that is located in a superior portion, posteriorly of an anterior-posterior centerline of the calf portion 110. The pivot aperture 148 is coaxial with the pivot apertures 128 in the medial thigh portions 114, 116 (FIG. 4). The fastening member 130, such as a pin or a rivet, passes through all of the coaxial apertures 128, 148 to pivotably secure the thigh portion 112 to the calf portion 110, as shown in FIG. 4.

An inferior end 150 of the posterior surface of the calf portion 110 provides a flexion stop surface 150. Thus, if a flexion stop member is disposed in one of the flexion stop apertures 124 in the thigh portion 112 (FIG. 4), contact between that flexion stop member and the flexion stop surface 150 limits further flexion of the hinge 30. In the illustrated embodiment, a plurality of flexion stop apertures 124 are provided so that the maximum flexion angle of the hinge 30 can be adjusted as desired by removing the flexion stop member from a first aperture 124 and disposing it within another aperture 124. For example, the flexion stop apertures 124 may be positioned to provide maximum flexion angles of 45°, 60°, 75° and 90°.

With particular reference to FIG. 9, a superior end 152 of the calf portion 110 includes a shoulder 154 that faces substantially in the posterior direction. The shoulder 154 provides an extension stop surface 154. Thus, if an extension stop member is disposed in one of the extension stop apertures 126 in the thigh portion 112 (FIG. 4), contact between that extension stop member and the extension stop surface 154 limits further extension of the hinge 30. In the illustrated embodiment, a plurality of extension stop apertures 126 are provided so that the maximum extension angle of the hinge 30 can be adjusted as desired by removing the extension stop member from a first aperture 126 and disposing it within another aperture 126. For example, the extension stop apertures 126 may be positioned to provide maximum extension angles of 40°, 30°, 20°, 10° and 0°.

With reference to FIGS. 1, 2 and 13-18, the medial pivot member 130 does not lie on the same axis with the lateral pivot member 132. Thus, the pivot axis of the medial hinge 30 does not coincide with the pivot axis of the lateral hinge 32. Because of this offset, as the wearer's leg flexes, the thigh frame 36 and calf frame 38 rotate relative to one another about both a horizontal flexion-extension axis $A_{F-E}$ and a vertical tibial rotation axis $A_{TR}$ (FIGS. 1 and 2).

Furthermore, neither hinge pivot axis coincides with the flexion-extension axis (represented by the "+" in FIGS. 13-18), which remains fixed throughout the flexion and/or extension of the knee. In the medial hinge 30 (FIGS. 16-18) the hinge pivot axis (which coincides with the pivot member 130) is located slightly superior and anterior to the flexion-extension axis, causing the flexion-extension axis to shift anterior relative to the pivot axis when the hinge 30 flexes. In the lateral hinge 32 (FIGS. 13-15) the hinge pivot axis (which coincides with the pivot member 132) is located slightly inferior and posterior to the flexion-extension axis, causing the flexion-extension axis to shift posterior relative to the pivot axis when the hinge 32 flexes. Thus, the medial side 42 of the thigh frame 36 moves anteriorly relative to the calf frame 38 (FIGS. 1, 2 and 16-18), and the lateral side 44 of the thigh frame 36 moves posteriorly relative to the calf frame 38 (FIGS. 1, 2 and 13-15) during knee flexion. Additionally, since the tibial rotation axis $A_{TR}$ is located nearer the medial side of the wearer's knee, the lateral hinge 32 has a larger translation component as compared to the medial side (FIGS. 13-18). As the wearer's knee extends, the motion described above is reversed.

Because the thigh frame 36 and calf frame 38 rotate relative to one another about the vertical tibial rotation axis $A_{TR}$, the calf portions 52, 110 of the hinges 30, 32 pivot relative to the calf frame 38 as the brace 34 flexes and extends (FIGS. 1 and 2). The pivot limits of the calf portions 52, 110 relative to the calf frame 38 are defined by the interaction of the sleeves 88, 140 and the faceted projections 76, 134, as described above. The ability of the calf portions 52, 110 to pivot relative to the calf frame 38 eliminates stresses that would otherwise develop in the hinges 30, 32 as the thigh frame 36 and calf frame 38 rotate relative to one another about the vertical tibial rotation axis $A_{TR}$.

The configuration of the interface between the calf portions 52, 110 and the calf frame 38 enables the relative pivoting about one axis, but no additional degrees of freedom. Thus, the brace 34 is still adapted to support the wearer's knee and provide restraint against harmful motions. This configuration is also advantageously independent of the spacing between the hinges 30, 32. Thus, this feature allows a single design to articulate smoothly on any range of patient sizes.

The embodiments of the brace hinges 30, 32 described above advantageously include only one pivot aperture 98, 148 in each hinge 30, 32. The absence of additional pivot apertures leaves free space available to accommodate the stop member apertures 66, 68, 124, 126. Adding the stop members to the brace 34 enables the brace 34 to be selectively limited in its range of motion. These range of motion limits enhance the ability of the brace 34 to protect the wearer's knee. Of course, as those of skill in the art will appreciate, the hinges 30, 32 could include additional pivot apertures without departing from the overall scope of the hinges 30, 32.

The embodiments described above also advantageously include flat hinge plates 56, 58, 74, 114, 116, 132. Flat hinge plates are inexpensive to manufacture, because they can be produced through, for example, stamping. Those of skill in the art will appreciate that the hinge plates 56, 58, 74, 114, 116, 132 could be of any non-flat shape without departing from the overall scope of the hinges 30, 32.

Figure 19:
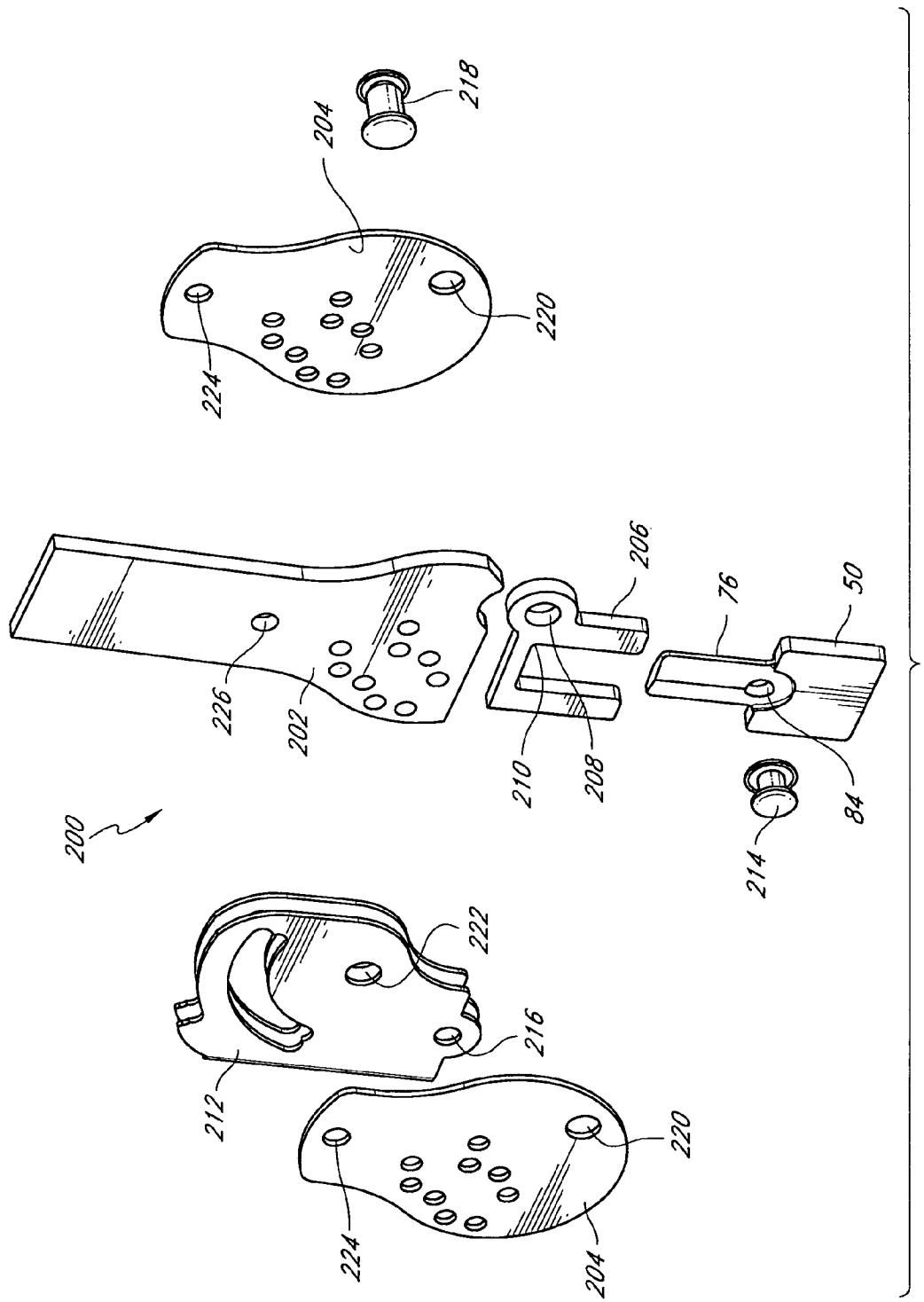
FIG. 19 is an exploded perspective view of an alternative embodiment of the lateral hinge of the brace of FIG. 1.
Figure 20:
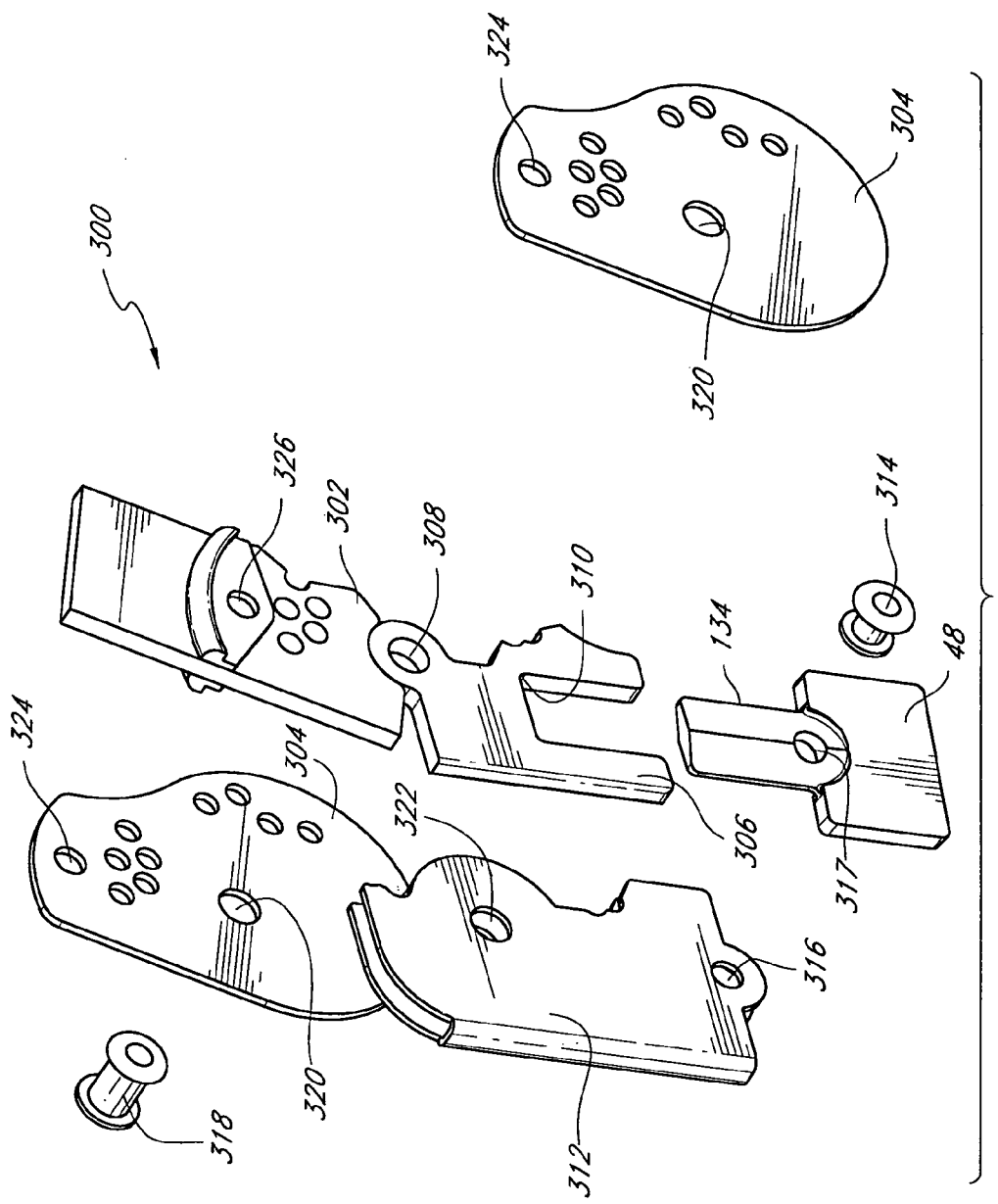
FIG. 20 is an exploded perspective view of an alternative embodiment of the medial hinge of the brace of FIG. 1.

FIGS. 19 and 20 illustrate alternative configurations of a lateral hinge 200, and a medial hinge 300, respectively. The lateral hinge 200 of FIG. 19 is similar in shape and function to the lateral hinge 32 of FIG. 3. The hinge 200 includes a three-piece thigh portion, including a center plate 202, and first and second outer plates 204. An inferior edge of the center plate 202 abuts a main plate portion 206 of the calf portion. The main plate portion 206 is shaped as an upside-down U, with a pivot aperture 208 attached to an outer edge of the posterior vertex 210. The main plate portion 202 straddles the faceted bar 76 atop the lateral upright 50, as in the lateral hinge 32 of FIG. 3. A sleeve 212, of similar shape to the sleeve 88 of FIG. 6, sandwiches the center plate 202, main plate portion 206 and faceted bar 76. A fastening member 214 extends through the inferior apertures 216, 84 in the sleeve 212 and faceted bar 76 to lock those components together. The outer plates 204 of the thigh portion abut outward facing surfaces of the sleeve 212, and a pivot member 218 extends through pivot apertures 208, 220, 222 in the main plate portion 206, on the outer plates 204, and on the sleeve 212 to lock these components together. Finally, securement apertures 224 on the outer plates align with a securement aperture 226 on the center plate 202, and a fastening member (not shown) extends through these apertures 224, 226 to secure them together.

The medial hinge 300 of FIG. 20 is similar in shape and function to the medial hinge 30 of FIG. 4. The hinge 300 includes a three-piece thigh portion, including a center plate 302, and first and second outer plates 304. An inferior edge of the center plate 302 abuts a main plate portion 306 of the calf portion. The main plate portion 306 is shaped substantially as an upside-down U, with a pivot aperture 308 attached to an outer edge of the posterior vertex 310. The main plate portion 306 straddles the faceted bar 134 atop the medial upright 48, as in the medial hinge 30 of FIG. 4. A sleeve 312, of similar shape to the sleeve 140 of FIG. 10, sandwiches the center plate 302, main plate portion 306 and faceted bar 134. A fastening member 314 extends through the inferior apertures 316, 317 in the sleeve 312 and faceted bar 134 to lock those components together. The outer plates 304 of the thigh portion abut outward facing surfaces of the sleeve 312, and a pivot member 318 extends through pivot apertures 308, 320, 322 in the main plate portion 306, on the outer plates 304, and on the sleeve 312, and to lock these components together. Finally, securement apertures 324 on the outer plates 304 align with a securement aperture 326 on the center plate 302, and a fastening member (not shown) extends through these apertures 324, 326 to secure them together.

SCOPE OF THE INVENTION

The above presents a description of the best mode contemplated for carrying out the present knee brace hinges having dual axes of rotation, and of the manner and process of making and using them, in such full, clear, concise, and exact terms as to enable any person skilled in the art to which they pertain to make and use these knee brace hinges. These knee brace hinges are, however, susceptible to modifications and alternate constructions from that discussed above that are fully equivalent. Consequently, these knee brace hinges are not limited to the particular embodiments disclosed. On the contrary, these knee brace hinges cover all modifications and alternate constructions coming within the spirit and scope of the knee brace hinges as generally expressed by the following claims, which particularly point out and distinctly claim the subject matter of the knee brace hinges.

What is claimed is:

1. A hinge mounted to an orthopedic knee brace, the hinge comprising:
    an upright including an elongate protrusion having a substantially diamond-shaped cross-section;
    a main plate portion, and a sleeve portion comprising first and second panels, the main plate portion including a recess for receiving the elongate protrusion, and the sleeve portion receiving the main plate portion and the elongate protrusion between the first and second panels.

2. The hinge of claim 1, wherein the upright is secured to a calf portion, and the main plate portion is connected to a thigh portion, wherein the thigh portion is pivotably secured to the calf portion.

3. The hinge of claim 2, wherein the thigh portion comprises first and second plates that receive the calf portion therebetween.

4. The hinge of claim 1, wherein the main plate portion is pivotable with respect to the upright about a longitudinal axis of the upright.

5. The hinge of claim 1, wherein the upright pivots with respect to the main plate portion about an axis that is substantially perpendicular to a flexion-extension axis of the knee brace.

6. An orthopedic knee brace in combination with the hinge of claim 1, comprising:
   a rigid calf frame; and
   a rigid thigh frame.

7. A hinge adapted to be mounted to a rigid upright of an orthopedic knee brace, the upright including an elongate protrusion having a substantially diamond-shaped cross-section, the hinge comprising:
   a hinge portion including a main plate portion and a sleeve portion, the main plate portion including a recess adapted to receive the protrusion, the sleeve portion receiving the main plate portion and the protrusion between first and second panels thereof;
   further comprising a fastening member extending through the first and second panels and through the protrusion to secure the hinge portion to the protrusion.

8. An orthopedic knee brace, comprising:
   a rigid frame including at least one of a rigid medial upright and a rigid lateral upright; and
   a hinge, the hinge including a portion secured to an end of the at least one upright;
   wherein the hinge portion is adapted to pivot relative to the at least one upright about an axis that is substantially perpendicular to a flexion-extension axis of the brace, wherein the at least one upright includes a protrusion shaped as a faceted bar;
   wherein the hinge portion includes a recess that receives the faceted bar;
   wherein the hinge portion is freely pivotable relative to the protrusion about a longitudinal axis of the protrusion until surfaces of a sleeve of the hinge portion contact surfaces of the faceted bar.

9. An orthopedic knee brace, comprising:
   a rigid thigh frame;
   a rigid calf frame;
   a medial hinge operably connecting a medial side of the thigh frame to a medial side of the calf frame, the medial hinge including a medial hinge portion operably secured to one of the thigh frame and calf frame; and
   a lateral hinge operably connecting a lateral side of the thigh frame to a lateral side of the calf frame, the lateral hinge including a lateral hinge portion operably secured to one of the thigh frame and calf frame;
   wherein the thigh frame and calf frame are adapted to pivot relative to one another simultaneously about a substantially horizontal flexion-extension axis and a substantially vertical longitudinal rotation axis as the brace flexes and/or extends, and the medial hinge portion and the lateral hinge portion are each adapted to pivot about substantially vertical axes relative to the one of the thigh frame and calf frame as the brace flexes and/or extends;
   wherein the lateral hinge comprises a main plate portion and a sleeve portion, the sleeve portion receiving the main plate portion between first and second panels thereof.

* * * * *